United States Patent [19]

Schwartz, deceased

[11] Plant 4,369

[45] Jan. 23, 1979

[54] ROSE PLANT

[75] Inventor: Ernest Schwartz, deceased, late of Kingsville, Md., by Hazel E. Schwartz, executrix

[73] Assignee: F. Harmon Saville Nor'East Miniature Roses, Rowley, Mass.

[21] Appl. No.: 855,015

[22] Filed: Nov. 25, 1977

[51] Int. Cl.[2] ..... A01H 5/00

[52] U.S. Cl. ..... Plt./10

[58] Field of Search ..... Plt./7, 10

*Primary Examiner*—Robert E. Bagwill
*Attorney, Agent, or Firm*—Vincent G. Gioia

[57] ABSTRACT

A novel rose variety of the miniature rose class characterized by its sprays of rose red flowers and particularly for the adaptability of the plant for pot forcing, substantially as shown and described.

1 Drawing Figure

The present invention relates to a new and distinct variety of rose plant of the miniature rose class, which was originated by my crossing as seed parent the floribunda rose known as "Zorina" and an unnamed seedling as pollen parent.

Among the novel characteristics possessed by this new variety which distinguish it from its parents and all other varieties of which I am aware are: (1) recurrent blooms of pleasing rose red coloring, and (2) produced on a plant of conspicuously abundant foliage but having the especially desirable characteristic of breaking readily from the soil. Asexual reproduction by budding of the new variety as performed in Essex County, Mass., shows that the foregoing and other distinguishing characteristics come true to form and are established and transmitted through succeeding propagations.

The new and improved rose variety which I have developed is a fine miniature rose of rose red coloring unusually superior as a greenhouse plant because of its "pot-forcing" qualities. The plant displays abundant attractive foliage and breaks readily from the soil thus producing a saleable plant relatively quickly. The flowers are usually borne in sprays and are of good petallage.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "53A" is plate 53A of the Royal Horticultural Society Color Chart.

Parentage: Seedling.
*Seed parent.*—"Zorina" (floribunda).
*Pollen parent.*—"Unnamed Seedling".
Class: Miniature.

The following observations are made of specimens grown outdoors in 30% shade in Essex County, Mass., during the month of October.

I. FLOWER

Blooming Habit: Recurrent.

A. *Bud.*—(1) Size: Medium (3/4-inch). (2) Form: Ovoid. (3) Color: When sepals first divide — 53A. When petals begin to unfurl — inside-outer edge 53B shading to 53C. Reverse side of petals — 53C. (4) Sepals: Short, smooth, some foliated. (5) Peduncle: Length — normal. Aspect — straight, sturdy. Strength — erect. Color — 44B.

B. *Bloom.*—(1) Size: Average size when fully expanded — about 1½ inch. (2) Borne: Usually in sprays 3 to 7 flowers, sometimes singly. (3) Form: Cupped, becoming flat upon opening, ruffled on maturity, reflex of edges only. (4) Petalage: Number of petals under normal conditions — about 30–35. (5) Color: (during first two days). Inner and outer petals at center of flower — 53B shading to 53C. Base of petals (point of attachment) — 11D. Reverse of petals — 52A. General tonality from a distance — rose red. (6) Color Change: As bloom ages — near to 46A, some bluing as blooms age — red and blue-red tones darkening first and then lightening — after three days shading to 47D.

C. *Petals.*—(1) Texture: Normal. (2) Appearance: Satiny on upper side, matte on underside. (3)Form: Fan shaped with rounded outside edge. (4) Arrangement: Regularly arranged, shingle-like, imbricated. (5) Petaloids in Center: Usually several. (6) Persistence: Petals persist. (7) Fragrance: None. (8) Lasting Quality: Very good on plant and as cut flower.

2. REPRODUCTIVE ORGANS

A. *Stamens, filaments and anthers.*—(1) Arrangement: Regularly arranged around styles. (2) Color: 17B.

B. *Pollen.*—Color — 17A.

C. *Styles.*—Even length, bunched — color 154D.

D. *Stigmas.*—Color — 154C.

E. *Hips.*—None observed.

3. PLANT

A. *Form.*—Upright, compact.

B. *Growth.*—Very vigorous, breaks readily from soil. Height attained — about 15 inches.

C. *Foliage.*—Compound 5 to 7 leaflets. (1) Size: Medium. (2) Quantity: Very abundant. (3) Color: New foliage: Upper side — near to 189A. Under side — near to and 191C. Old foliage: Upper side — 191A. Under side — 191B. (4) Shape: Oval, slightly elongated toward tip. (5) Texture: Matte. (6) Edge: Serrated. (7) Serration: Even. (8) Leaf Stem: Color — upper side — 146B; under side — 146D. (9) Stipules: Medium length, smooth. (10) Resistance to Disease: Blackspot — normal. Mildew — normal.

D. *Wood.*—(1) New wood: Color — near 138B. Bark — smooth. (2) Old wood: Color — 141C. Bark — smooth.

E. *Thorns.*—(1) Thorns: Quantity: few on stalks and laterals. (2) Prickles: Form — straight, long, thin, pointed widening at base. Color — when young — 48A; when mature — 166B. Position — random.

I claim:

1. A new and distinct variety of rose plant of the miniature class, substantially as shown and described, characterized particularly by recurrent rose red flowers borne usually in sprays on the plant especially well adapted for pot forcing due to its ability to break readily from the soil and having conspicuously abundant foliage.

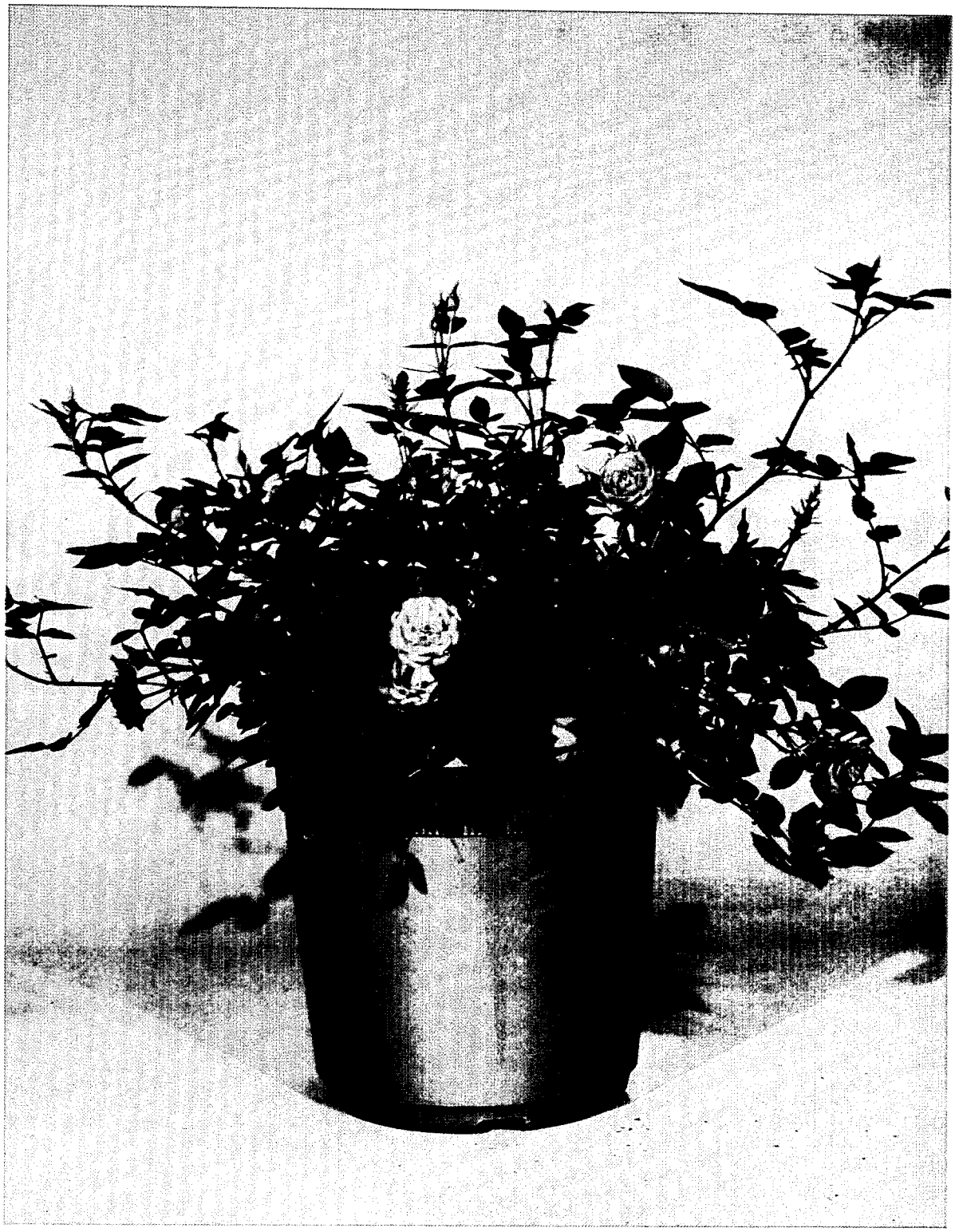

* * * * *